United States Patent [19]

Silber et al.

[11] Patent Number: 5,359,132

[45] Date of Patent: Oct. 25, 1994

[54] PROCESS FOR THE PREPARATION OF SODIUM SALTS OF AROMATIC SULPHINIC ACIDS CONTAINING NITRO GROUPS

[75] Inventors: Gunter Silber, Cologne; Gerold Schade; Udo Thiel, both of Leverkusen, all of Fed. Rep. of Germany

[73] Assignee: Bayer Aktiengesellschaft, Leverkusen, Fed. Rep. of Germany

[21] Appl. No.: 157,768

[22] Filed: Nov. 24, 1993

[30] Foreign Application Priority Data

Dec. 3, 1992 [DE] Fed. Rep. of Germany ....... 4240708

[51] Int. Cl.$^5$ ........................................... C07C 313/02
[52] U.S. Cl. .................................................. 562/125
[58] Field of Search ........................................ 562/125

[56] References Cited

FOREIGN PATENT DOCUMENTS 3302647 8/1984 Fed. Rep. of Germany .

OTHER PUBLICATIONS

*Organic Chemical Intermediates for Insecticides Fungicides and Rodenticides* FIAT Final Report No. 949, British Intelligence Objectives Subcommittee; Oct. 14, 1946; J. T. Thurston; Technical Industrial Intelligence Division U.S. Department of Commerce; 4 pages.

*Primary Examiner*—Nicky Chan
*Attorney, Agent, or Firm*—Sprung Horn Kramer & Woods

[57] ABSTRACT

Sodium salts of aromatic sulphinic acids containing nitro groups are obtained in particularly pure form and good yield by introducing the corresponding sulphonyl chlorides into an aqueous alkali metal sulphite solution which is at a temperature of $-10°$ to $45°$ C. and has a pH of 6 to 10, then cooling the suspension to $-10°$ to $0°$ C., then metering in sodium hydroxide solution in such a way that the temperature does not exceed $0°$ C. throughout the reaction, and then raising the temperature, maintaining stirring and simultaneously keeping the pH at 8 to 9 by the addition of sodium hydroxide solution.

5 Claims, No Drawings

PROCESS FOR THE PREPARATION OF SODIUM SALTS OF AROMATIC SULPHINIC ACIDS CONTAINING NITRO GROUPS

The invention relates to a process for the preparation of sodium salts of aromatic sulphinic acids containing nitro groups by reacting the corresponding sulphonyl chlorides with alkali metal sulphite in the presence of sodium hydroxide solution.

Sodium salts of aromatic sulphinic acids containing nitro groups can for example be alkylated to give the corresponding sulphones, which can in turn be used as intermediates for the preparation of reactive dyes.

It is known to prepare sodium sulphinates by adding the sulphonyl chloride to an aqueous sodium sulphite solution over several hours at 10° to 70° C. and simultaneously adding sodium hydroxide solution to keep the reaction medium alkaline (FIAT Final Report 949, p. 23 to 24). In another process, the sulphonyl chloride and sodium hydroxide solution are added simultaneously to a mixture of sodium hydrogensulphite, sodium hydroxide solution, phosphoric acid and water over 2 hours at 60° C. (German Offenlegungsschrift 33 02 647, Example 17).

The disadvantage of these processes is that sodium sulphinates prepared in this way are obtained in a yield of only ca. 80% and always contain 4 to 6% by weight of the corresponding sodium sulphonates, which are formed in a secondary reaction by hydrolysis of the sulphonyl chlorides and subsequent neutralisation of the resulting sulphonic acids.

This content of sodium sulphonates is unwanted, on the one hand because it reduces the yield of the desired sodium sulphinate and on the other hand because it can lead to additional effluent pollution when the sulphinates are processed further in an aqueous medium.

It has now been found that if the reaction conditions are chosen appropriately, the sodium salts of aromatic sulphinic acids containing nitro groups can be prepared in excellent yield and with high purity.

The invention therefore provides a process for the preparation of compounds of the formula

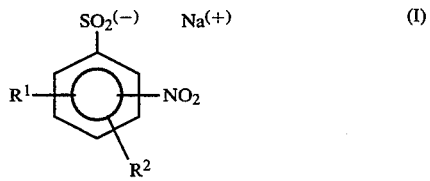

in which $R^1$ and $R^2$ independently of one another are hydrogen, $C_1-C_6$-alkyl, $C_5-C_7$-cycloalkyl, halogen, $C_6-C_{12}$-aryl, $C_6-C_{18}$-aralkyl, $C_1-C_6$-alkoxy, $C_6-C_{12}$-aryloxy, amino, $C_2-C_5$-acylamino or carboxy, by the reaction of sulphonyl chlorides of the formula

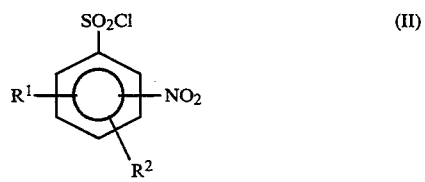

in which $R^1$ and $R^2$ are as defined above, with alkali metal sulphite in the presence of sodium hydroxide solution, characterised in that the sulphonyl chloride (II) is introduced into an aqueous alkali metal sulphite solution which is at a temperature of −10° to 45° C., preferably −5° to 40° C. and has a pH of 6 to 10, preferably 6 to 9, the suspension—if its temperature is above 0° C.—is cooled to −10° to 0° C. preferably −5° to 0° C., and sodium hydroxide solution is then metered in in such a way that the temperature does not exceed 0° C. for at least 80%, preferably at least 90%, of the reaction time. Then, to effect an after-reaction or the formation of the sodium salt, the temperature can be raised to 10° to 80°, preferably 15° to 60° C., the pH preferably being kept at 8-10, especially 8-9, by the addition of sodium hydroxide solution.

The alkyl radicals ($R^1$ and/or $R^2$) can be linear or branched. They preferably contain 1 to 4 carbon atoms. Examples of suitable alkyl radicals are methyl, ethyl, propyl, isopropyl, butyl, isobutyl, pentyl, isopentyl, hexyl and isohexyl.

Preferred cycloalkyl radicals ($R^1$ and/or $R^2$) include cyclopentyl and, in particular, cyclohexyl.

Halogen ($R^1$ and/or $R^2$) includes iodine and, preferably, fluorine, chlorine and bromine.

Aryl ($R^1$ and/or $R^2$) preferably includes phenyl and tolyl.

Examples of suitable aralkyl radicals ($R^1$ and/or $R^2$) are those having 6 to 18 carbon atoms whose aliphatic moiety contains 1 to 6 carbon atoms and whose aromatic moiety is a radical from the benzene series. Preferred examples include β-phenyl-ethyl, γ-phenyl-propyl and β-phenyl-n-hexyl, especially benzyl.

Alkoxy radicals ($R^1$ and/or $R^2$) include linear and branched radicals preferably having 1 to 4 C atoms, e.g. methoxy, ethoxy, propoxy, isopropoxy, butoxy and isobutoxy.

Aryloxy is preferably phenoxy and acylamino is preferably acetylamino.

Sulphonyl chlorides which are preferred as starting compounds have formula (II) in which $R^1$ and $R^2$ independently of one another are hydrogen, an alkyl radical having 1 to 4 carbon atoms, fluorine, chlorine, bromine, phenyl, methoxy, ethoxy, phenoxy or acetylamino, e.g.
o-nitrobenzenesulphonyl chloride,
m-nitrobenzenesulphonyl chloride,
p-nitrobenzenesulphonyl chloride,
2-methyl-5-nitro-benzenesulphonyl chloride,
4-methyl-3-nitro-benzenesulphonyl chloride,
2-ethyl-5-nitro-benzenesulphonyl chloride,
2,4-dimethyl-3-nitro-benzenesulphonyl chloride,
2-chloro-5-nitro-benzenesulphonyl chloride,
4-chloro-3-nitro-benzenesulphonyl chloride,
2-methoxy-5-nitro-benzenesulphonyl chloride,
4-methoxy-3-nitro-benzenesulphonyl chloride and
4-acetylamino-3-nitro-benzenesulphonyl chloride.

In terms of the invention, the expression "alkali metal sulphite" also includes alkali metal hydrogensulphites.

Examples of suitable aqueous alkali metal sulphite solutions are 15 to 40% by weight aqueous solutions of an alkali metal sulphite or alkali metal hydrogensulphite. Solutions of sodium sulphite or sodium hydrogensulphite are preferred. As an example, 3 to 10 parts by weight of the alkali metal sulphite solution can be used per part by weight of the sulphonyl chloride. It may be necessary to add an alkali (e.g. sodium hydroxide solution) or an acid (e.g. hydrochloric acid) in order to bring the pH within the range 6 to 10. In general, additions of alkali are required when using hydrogensulphites.

The sodium hydroxide solution can have a concentration of 30 to 60% by weight, for example. Sodium hydroxide solution having a concentration of 45 to 50% by weight is preferred. The rate of introduction of the sodium hydroxide solution is regulated so that the heat of reaction evolved can be dissipated without the reaction mixture exceeding a temperature of 0° C.

It is not necessary, on the other hand, to maintain a particular pH during the metering of the sodium hydroxide solution. Rather, the pH can vary within wide limits, for example between 3 and 7, during the reaction.

When the reaction is complete, the reaction mixture can be worked up in a manner known per se: For example, a possible procedure is to heat the reaction mixture to 40° to 95° C., preferably 40° to 70° C., said reaction mixture optionally being diluted by the addition of water and the pH optionally being adjusted to e.g. 8 to 12, preferably 8 to 11.5, by the addition of sodium hydroxide solution.

After subsequent clarification by filtration, if necessary, the product can be precipitated by cooling, optionally with the addition of sodium chloride, and isolated in known manner, e.g. by filtration.

Sodium salts of aromatic sulphinic acids containing nitro groups, prepared according to the invention, generally contain less than 1% by weight of the corresponding sulphonic acid and are generally obtained in a yield of well over 90% of theory.

EXAMPLES

Example 1

67 ml of 50% by weight sodium hydroxide solution were added to a solution of 184 g of sodium hydrogensulphite in 649 ml of water, bringing the pH to 6.4. The mixture was then cooled to −5° C. and 2-chloro-5-nitro-benzenesulphonyl chloride in moist form (water content 20% by weight, 256 g of 100% 2-chloro-5-nitro-benzenesulphonyl chloride) was added all at once.

100 ml of 50% by weight sodium hydroxide solution were then introduced in such a way that the temperature could be kept in the range −5° to 0° C. by cooling. The pH was then adjusted to 8 to 9 with sodium hydroxide solution and the mixture was subsequently stirred for 30 minutes at −5° to 0° C. The product was converted to the sodium salt by heating to 15° C. and simultaneously keeping the pH in the range 8–9 by the addition of 18 ml of 50% by weight sodium hydroxide solution. Stirring was continued for 30 minutes.

The mixture was then heated to 60° C., 2 g of filter aid (®Célite) were added and the resulting mixture was filtered.

Finally, 440 g of rock salt were added, the mixture was cooled to 20° C. and sodium 2-chloro-5-nitro-benzenesulphinate was isolated by filtration in a yield of 95% in the form of a moist filter cake (water content 50% by weight), the sodium 2-chloro-5-nitro-benzenesulphonate content being 0.8% by weight.

Example 2

Comparative Example 70 ml of 50% by weight sodium hydroxide solution were added to a solution of 184 g of sodium hydrogensulphite in 649 ml of water, bringing the pH to 6.6. The mixture was then cooled to 20° C. and 2-chloro-5-nitro-benzenesulphonyl chloride in moist form (water content 20% by weight, 256 g of 100% 2-chloro-5-nitro-benzenesulphonyl chloride) was added all at once.

112 ml of 50% by weight sodium hydroxide solution were then introduced in such a way that the temperature could be kept in the range 20° to 22° C. by cooling. The pH was then adjusted to 10.5 with sodium hydroxide solution and the mixture was subsequently stirred for 30 minutes at 20° to 22° C. during which time the pH was kept in the range 10 to 11 by the addition of a further 2 ml of 50% by weight sodium hydroxide solution. The mixture was then heated to 60° C. and filtered. Finally, 440 g of rock salt were added, the mixture was cooled to 20° C. and sodium 2-chloro-5-nitro-benzenesulphinate was isolated by filtration in a yield of 82.2% of theory in the form of a moist filter cake (water content 50% by weight).

Example 3

Comparative Example

The starting materials were a sodium sulphite solution, made up of 2400 kg of sodium hydrogensulphite (30% by weight) and 5700 l of water, and 450 l of sodium hydroxide solution (50% by weight). The sodium sulphite solution was adjusted to pH 8.5 with sodium hydroxide solution and cooled to 10° C. Then 2000 kg of 2-chloro-5-nitro-benzenesulphonyl chloride in moist form (water content 30% by weight) and 574 l of 50% by weight sodium hydroxide solution were simultaneously introduced at 10° to 18° C. over 6 hours, the pH being kept at about 8 to 9 throughout. The mixture was subsequently stirred for a further 120 minutes and then worked up as described in Example 1.

Sodium 2-chloro-5-nitro-benzenesulphinate was obtained in a yield of 83% of theory.

Example 4

70 ml of 50% by weight sodium hydroxide solution were added to a solution of 194 g of sodium hydrogensulphite in 666 ml of water, bringing the pH to 6.4. The mixture was then cooled to −5° C. and 2-methyl-5-nitro-benzenesulphonyl chloride in moist form (water content 20% by weight, 236 g of 100% 2-methyl-5-nitro-benzenesulphonyl chloride) was added all at once.

120 ml of 50% by weight sodium hydroxide solution were then introduced in such a way that the temperature could be kept in the range −5° to 0° C. by cooling. The pH was then adjusted to 8 to 9 with 28 ml of 50% by weight sodium hydroxide solution and the mixture was subsequently stirred for 30 minutes at −5° to 0° C. It was then heated to 25° C. to cause salting-out, and stirring was continued for a further 30 minutes.

Finally, 440 g of rock salt were added, the mixture was cooled to 20° C. and sodium 2-methyl-5-nitro-benzenesulphinate was isolated by filtration in a yield of 93% in the form of a moist filter cake (water content 50% by weight), the 2-methyl-5-nitro-benzenesulphonic acid content being 0.8% by weight.

We claim:

1. In the preparation of a compound of the formula

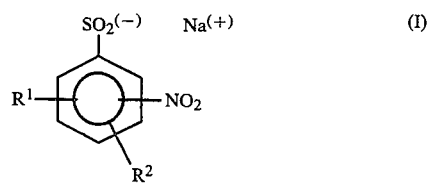

in which $R^1$ and $R^2$ independently of one another are hydrogen, $C_1$-$C_6$-alkyl, $C_5$-$C_7$-cycloalkyl, halogen, $C_6$-$C_{12}$-aryl, $C_6$-$C_{18}$-aralkyl, $C_1$-$C_6$-alkoxy, $C_6$-$C_{12}$-aryloxy, amino, $C_2$-$C_5$-acylamino or carboxy, by reacting a sulphonyl chloride of the formula

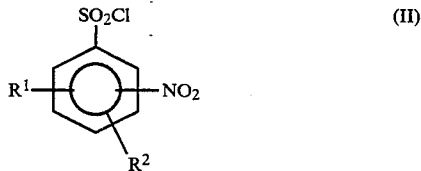

(II)

with an alkali metal sulphite in the presence of sodium hydroxide solution, the improvement which comprises introducing the sulphonyl chloride (II) into an aqueous solution of the alkali metal sulphite which is at a temperature of −10° to 45° C. and has a pH of 6 to 10, thereby to form a suspension, if the temperature of the suspension is above 0° C. cooling the suspension to −10° to 0° C., and then metering sodium hydroxide solution into the suspension in such a way that the temperature does not exceed 0° C. for at least 80% of the reaction time.

2. A process according to claim 1, wherein the sulphonyl chloride (II) is introduced into the aqueous alkali metal sulphite solution which is at a temperature of −5° to 40° C.

3. A process according to claim 1, wherein the sulphonyl chloride (II) is introduced into the aqueous alkali metal sulphite solution which has a pH of 6 to 9.

4. A process according to claim 1, wherein the temperature of the suspension when first formed is above 0° C., the suspension is then cooled to −5° to 0° C., and the sodium hydroxide solution is then metered in.

5. A process according to claim 1, wherein the sodium hydroxide solution is metered in in such a way that the temperature does not exceed 0° C. for at least 90% of the reaction time.

* * * * *